United States Patent [19]

Friswell

[11] Patent Number: 5,100,623

[45] Date of Patent: Mar. 31, 1992

[54] LABORATORY EVAPORATION APPARATUS

[75] Inventor: David R. Friswell, Holliston, Mass.

[73] Assignee: Zymark Corporation, Hopkinton, Mass.

[21] Appl. No.: 425,081

[22] Filed: Oct. 23, 1989

[51] Int. Cl.⁵ .......................................... G01N 21/00
[52] U.S. Cl. .................................. 422/68.1; 422/81; 422/102; 422/261; 436/177; 34/54; 159/16.1
[58] Field of Search ............... 422/68.1, 81, 102, 261, 422/278; 436/177, 181; 34/54; 203/1, 49, 50; 202/181; 159/16.1; 210/180, 188, 85

[56] References Cited

U.S. PATENT DOCUMENTS

| | | | |
|---|---|---|---|
| 4,600,473 | 7/1986 | Friswell | 422/100 |
| 4,668,636 | 5/1989 | Ringrose et al. | 422/102 |
| 4,815,978 | 3/1989 | Mazza et al. | 422/100 |

Primary Examiner—Robert J. Warden
Assistant Examiner—Laura E. Collins
Attorney, Agent, or Firm—John E. Toupal; Harold G. Jarcho

[57] ABSTRACT

An apparatus for use in isolating solids from liquids by evaporating the liquid, including a vessel for receiving a composition of liquid and solid substances; a gas supply for supplying a drying gas; a gas line for directing the drying gas from the gas supply to the vessel; a liquid supply for supplying a solvent capable of dissolving the solid substance; and a liquid line for directing the solvent from the liquid supply to the vessel. Also included is a sensing means for sensing conditions of evaporation within the vessel and an automatic control system adapted to sequentially initiate a flow of drying gas to the vessel, initiate a flow of solvent to the vessel in response to sensing of a given evaporation condition by the sensing means, interrupt the flow of solvent to the vessel after a certain quantity of solvent has been received thereby, and interrupt the flow of drying gas to the vessel in response to sensing of a particular evaporation condition by the sensing means. The apparatus automatically produces an evaporation cycle, a solvent reconstitution cycle, and a re-evaporation cycle thereby significantly reducing previously required costly manual procedures.

14 Claims, 2 Drawing Sheets

LABORATORY EVAPORATION APPARATUS

BACKGROUND OF THE INVENTION

This invention relates generally to laboratory evaporation apparatus and, more particularly, to apparatus for automatically and sequentially isolating a solid in a sample by evaporating its liquid content, reconstituting the residue as a liquid by adding a solvent, and again isolating the solid by evaporating the added solvent.

In many laboratory applications, it is desirable to transfer a solute from one solvent system to another solvent system. For example, this procedure is used frequently in liquid chromatography where a solution, perhaps a liquid fraction obtained from one chromatographic procedure, can be more specifically analyzed by use of a different solvent. In the past, it has been common to place the first solution into a tube and, using a gas sparge tube, or cannula, contact the solution with sufficient drying gas to remove the unwanted liquid.

An improved system for achieving laboratory evaporation is disclosed in U.S. Pat. No. 4,707,452. That system provides a receptacle for liquid being processed and gas feed means to supply carrier gas into the receptacle such that the gas follows a path downwardly along the receptacle wall until it reaches the material to be treated. This procedure serves to leave a relatively free central path in the receptacle through which the process gas, now laden with any material being evaporated, may proceed upwardly through the central portion of the volume enclosed by the walls of the receptacle. Because the gas leaving the receptacle is not much diluted by mixing with the incoming gas, it is more sensitive to analysis by any number of procedures. However, after evaporation is completed, much of the residue usually is spread in a thin film over the inside surface of the receptacle. Full residue recovery, therefore, generally requires one or more solvent adding reconstitution steps followed by further evaporation. Such procedures are time consuming for highly trained laboratory personnel.

The object of this invention, therefore, is to provide an improved, more efficient apparatus for accomplishing various types of laboratory evaporation procedures.

SUMMARY OF THE INVENTION

For use in isolating solids from liquids by evaporating the liquid, the invention is an apparatus including a vessel for receiving a composition of liquid and solid substances; a gas supply for supplying a drying gas; a gas line for directing the drying gas from the gas supply to the vessel; a liquid supply for supplying a solvent capable of dissolving the solid substance; and a liquid line for directing the solvent from the liquid supply to the vessel. Also included is a sensing means for sensing conditions of evaporation within the vessel and an automatic control system adapted to sequentially initiate a flow of drying gas to the vessel, initiate a flow of solvent to the vessel in response to sensing of a given evaporation condition by the sensing means, interrupt the flow of solvent to the vessel after a certain quantity of solvent has been received thereby, and interrupt the flow of drying gas to the vessel in response to sensing of a particular evaporation condition by the sensing means. The apparatus automatically produces an evaporation cycle, a solvent reconstitution cycle, and a re-evaporation cycle thereby significantly reducing previously required costly manual procedures.

According to one feature of the invention, the apparatus further includes a gas valve for controlling the flow of drying gas between the gas supply and the vessel; a liquid valve for controlling the flow of solvent between the liquid supply and the vessel; and the control system is operatively coupled to the gas valve, the liquid valve, and the sensing means, and is adapted to sequentially open the gas valve to initiate the flow of drying gas, open the liquid valve to initiate the flow of solvent, close the liquid valve to interrupt the flow of solvent, and close the gas valve to interrupt the flow of drying gas. The provision of automatically controlled gas and liquid valves facilitates the evaporation process.

According to another feature of the invention, the control system is further adapted to close the gas valve and interrupt the flow of drying gas to the vessel in response to sensing of the given condition; and to open the gas valve and initiate the flow of drying gas to the vessel means after the certain quantity of solvent has been received by the vessel. This feature automatically terminates drying gas flow during the reconstitution cycle.

According to yet another feature of the invention, the apparatus includes an actuator coupled to the control system and activatable thereby into either an active mode wherein the liquid supply provides pressurized solvent to the liquid valves or an inactive mode wherein the liquid supply means fails to provide pressurized solvent to the liquid valves; and the control system is further adapted to produce the active mode during substantially all periods in which the liquid valves are open and to produce the inactive mode during substantially all periods in which the liquid valves are closed. Elimination of activating pressure during the inactive mode insures against inadvertent release of solvent and reduces wear on the liquid valves.

According to a further feature of the invention, the apparatus includes a nozzle for discharging fluid into the vessel; and the nozzle is in fluid communication with both the gas line and the liquid line means so as to receive therefrom, respectively, either drying gas or solvent for discharge into the vessel. The use of a single nozzle for both drying and reconstitution cycles simplifies the structural requirements of the apparatus.

According to other features of the invention, the liquid supply comprises a pressurizable supply container having a pressure inlet and a discharge outlet connected to the liquid valve, the actuator comprises a pressure valve for providing pressure at the inlet in said active mode and eliminating pressure at the inlet in the inactive mode and the pressure valve is connected for fluid communication between the inlet and the gas supply. Dual use of the gas supply for both supplying drying gas and pressurizing the liquid supply further simplifies the component requirements of the apparatus.

In accordance with another feature of the invention, the vessel is a tubular vessel, and the nozzle is positioned to direct the solvent in a helical path at an angle of from about 30 to 45 angular degrees downwardly along an interior wall of the vessel. Helical discharge of solvent enhances removal of residue from the vessel's inner wall during the reconstitution cycle.

According to an additional feature, the vessel has an upper portion with a substantially uniform cross-section having one area and a lower portion with a substantially uniform cross-section of substantially smaller area and the sensing means includes a source disposed to direct a beam of radiation through the lower portion of the vessel; a radiation detector disposed to receive the beam of radiation directed through the lower portion of the vessel; and an electrical control for controlling the flow of drying gas between the gas supply and the gas line in response to the level of radiation detected by the detector. The provision of a specially configured vessel, a radiation source and a radiation detector facilitates accurate monitoring of the evaporation process.

According to still other features of the invention, the apparatus comprises a plurality of vessels, a plurality of gas valves each adapted to control the flow of drying gas to a different one of the vessels, and a plurality of liquid valves each adapted to control the flow of solvent to a different one of the vessels. The provision of plural components permits the automatic and simultaneous evaporation of plural samples.

Another invention is a unique process for collecting solid residue produced in a tubular vessel by evaporating the liquid from a composition of liquid and solid substances and comprising the steps of: causing a solvent capable of dissolving the solid residue to flow into the vessel through an inlet which directs the flow of the solvent in a generally helical flow pattern extending along the wall of the vessel in a direction from an upper portion thereof toward a lower portion thereof thereby washing the residue on the wall to the bottom of the vessel; and then evaporating the solvent so as to isolate the solid residue in the vessel. Provision of a helical flow pattern enhances the washing of residue from the vessel's inner wall during the reconstitution process.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
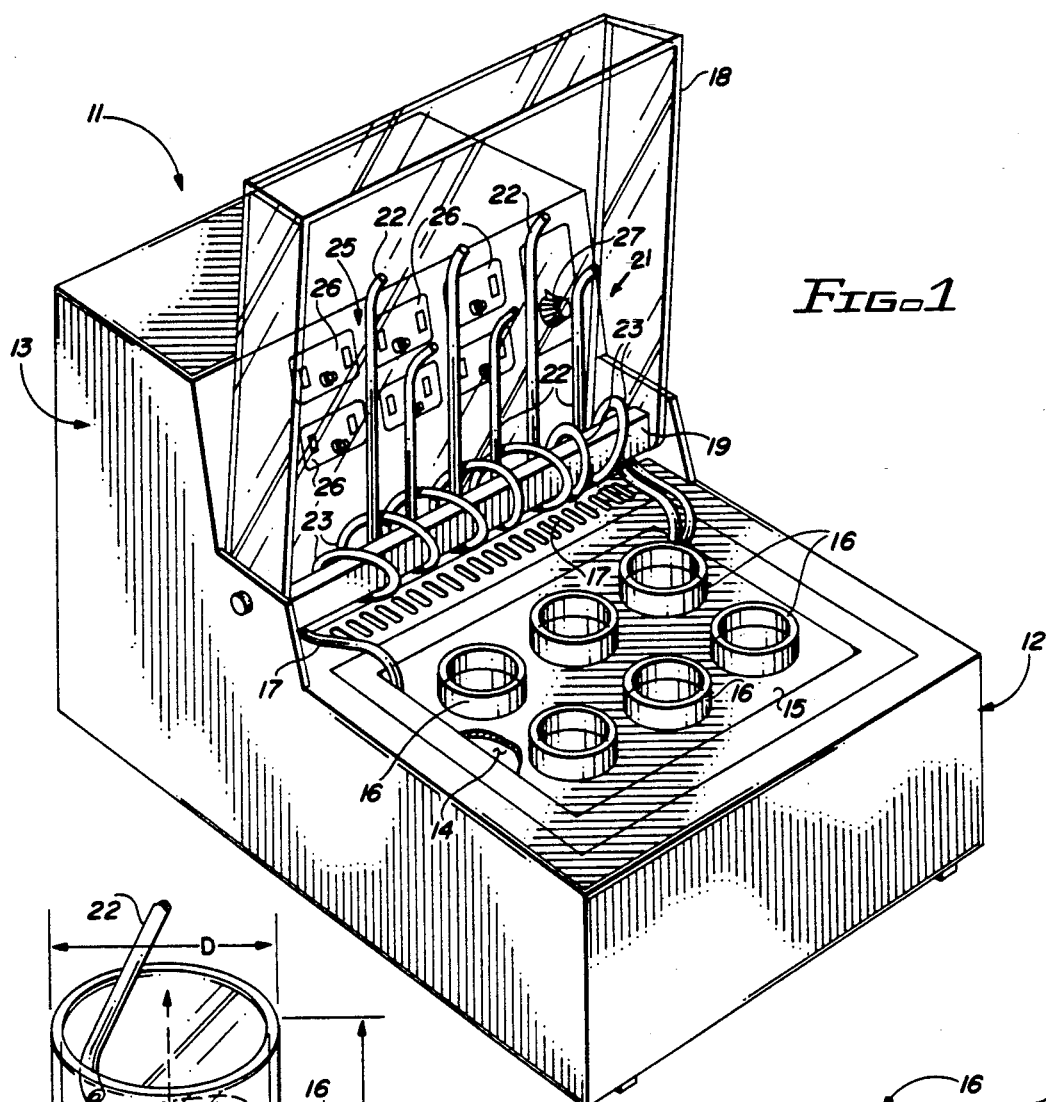
FIG. 1 is a perspective view of an automatic evaporator apparatus according to the invention.

An evaporator 11 is encompassed in a housing including a front housing portion 12 and a rear housing portion 13. Defined by the front portion 12 is a hollow basin 14 for accommodating a temperature controllable water bath. A support rack 15 is mounted in the basin 14 and retains a plurality of vessels 16 having openings at their upper ends for receiving liquid and solid compositions. Also defined by the front housing portion 12 is a vent 17 that communicates through an exhaust fan (not shown) with an exhaust port (not shown) in the rear housing portion 13.

A tray-shaped, transparent cover 18 is pivotally mounted on the rear housing portion 13 and can be pivoted from an open position shown in FIG. 1 into a closed position completely covering the basin 14 and the vent 17. Mounted in a rear portion of the cover 18 is a bracket assembly 19 that supports a combined gas and liquid supply line assembly 21. Included in the supply line 21 assembly are a plurality of elongated nozzles 22 rigidly supported by the bracket 19. Upon closure of the cover 18, each of the nozzles 22 is arranged to enter the open top of a different one of the vessels 16 in the manner shown in FIG. 2. A plurality of flexible tubes 23 provide fluid communication between the nozzles 22 and gas and liquid supply mechanisms (FIG. 4) mounted within the rear housing portion 13.

An electrical control system (FIG. 4) is retained within the rear housing portion 13 and automatically controls a predetermined evaporation process in each of the vessels 16 as described in greater detail hereinafter. Supported on the rear housing portion 13 is a control panel 25 having a plurality of panel sections 26 each dedicated to a different one of the vessels 16. Each of the panel sections 26 retains manual switches and indicator lamps for selecting and monitoring an evaporation process performed in the vessel 16 associated therewith. Also retained in the control panel 25 is a manual control 27 for selecting the temperature of a water bath within the basin 14.

Figure 2:
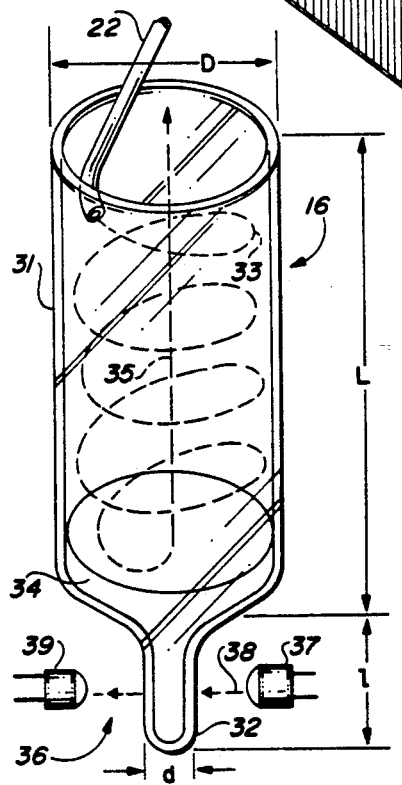
FIG. 2 is a detailed view of an individual evaporator vessel and sensing system used in the apparatus of FIG. 1.

The vessels 16 are all identical and one is depicted more clearly in FIG. 2. Each vessel 16 includes a tubular upper portion 31 having a diameter D and a length L and a lower portion 32 having a diameter d and a length l. As shown in FIG. 2, both the diameter D and the length L of the upper portion 31 are substantially greater, respectively, than the diameter d and the length l of the lower portion 32. Thus, the area defined by a cross-section through the lower portion 32 is substantially smaller than the area defined by a cross-section through the upper portion 31. Also illustrated in FIG. 2 is one of the nozzles 22 positioned at the top of the upper tube portion 31. It will be understood that upon closure of the cover 18 (FIG. 1) one of the nozzles 22 will be similarly positioned within each of the vessels 16. Preferably, the disposition of the nozzle 22 is such as to produce fluid discharge in a helical path 33 along the inner wall of the upper vessel portion 31 downwardly at an angle of from about 30 to 45 degress from horizontal. Because of the helical flow, a vortexing action occurs in the liquid content 34 of the vessel 16 producing sample homogeneity and continuous rinsing of the vessels inner wall. After reaching the bottom of the vessel 16, the vapor-laden drying gas exits via an unobstructed path 35 up the center portion of the vessel 16 and is removed by an exhaust fan (not shown) through the vent 17 (FIG. 1). Further details relating to the positioning and operation of the discharge nozzle 22 are disclosed in above noted U.S. Pat. No. 4,707,452.

Figure 3:
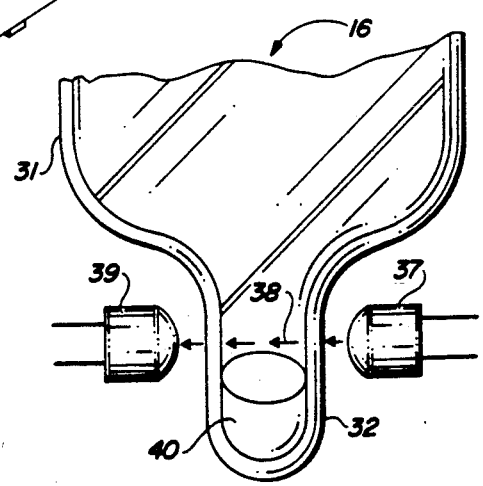
FIG. 3 is a view identical to that shown in FIG. 2 after completion of an evaporation cycle.

Also shown in FIG. 2 is a sensing system 36 for monitoring completion of an evaporation cycle within the vessel 16. The sensing system 36 comprises a source 37 for directing a beam of radiation 38 through the lower vessel portion 32 and a detector 39 positioned to receive the beam 38. Preferably, the source 37 comprises a light source and the detector 39 is a photodetector. Prior to completion of an evaporation cycle, the existence of liquid sample in the lower vessel portion 32 focuses the transmission of the beam 38 between the source 37 and the detector 39 which thereby produces an output. However, upon completion of the evaporation process a solid or liquid residue 40 in the lower vessel portion 32 lies below the light beam 38 as shown in FIG. 3. The resultant decreased level of transmission through the lower vessel portion 32 causes the detector 39 to change the output signal indicating a completion of the evaporation process.

When evaporation is completed within a vessel 16, most of the residue will be deposited at the bottom of a lower vessel portion 32 as shown in FIG. 3. However, some portion of the residue will be spread in a thin film over an inner surface of the upper vessel portion 31. Collection of that residue portion is accomplished by discharging through the nozzle 22 a solvent capable of dissolving the residue. Because of the geometrical relationship between the nozzle 22 and the vessel 16, the solvent is discharged in the helical path 33 (FIG. 2) ensuring a thorough washing of residue from the inner wall of the upper vessel portion 31. The solvent added to the vessel during the washing process then is separated from the desired solid residue by a repeat of the above described evaporation process.

Figure 4:
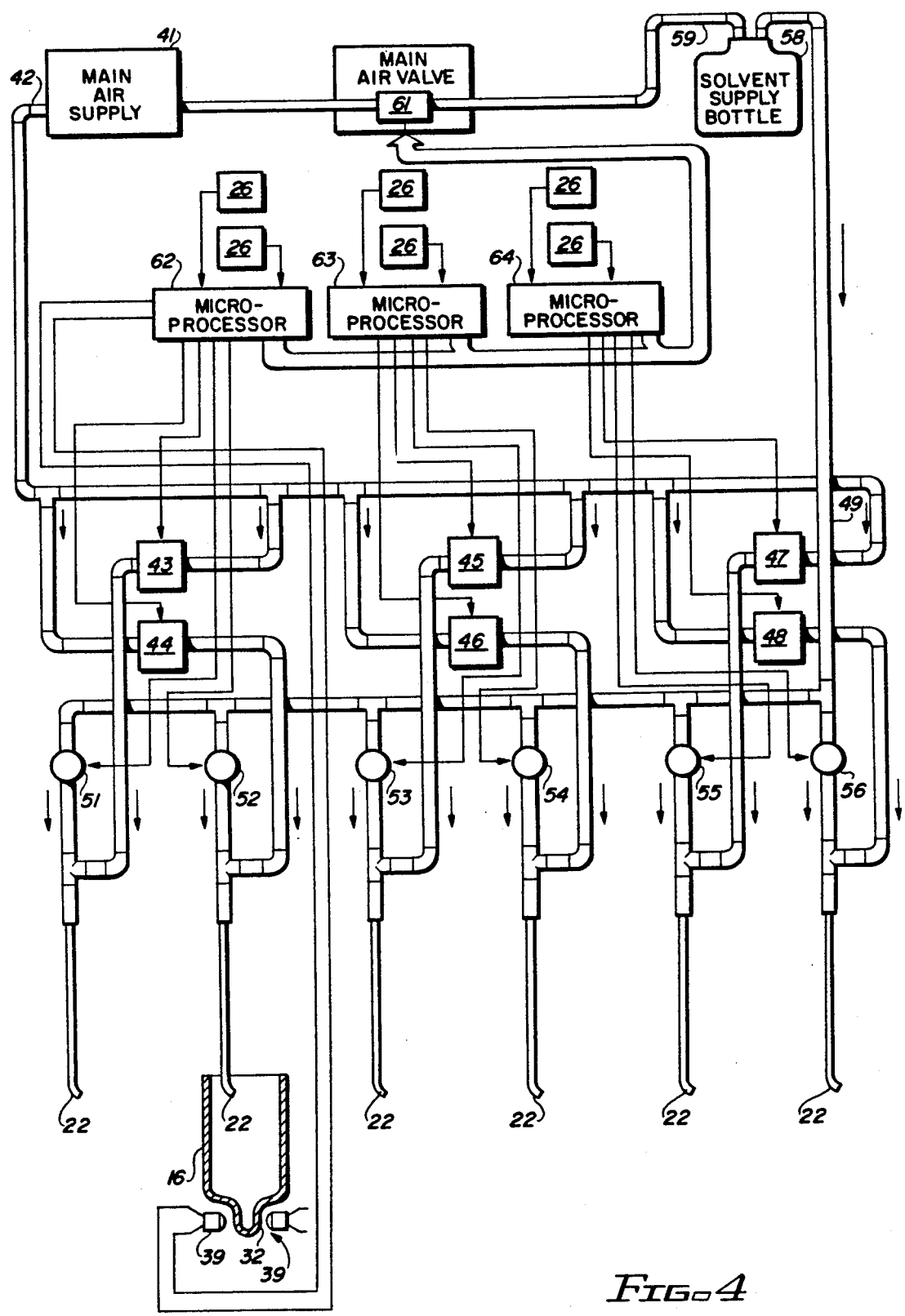
FIG. 4 is a schematic diagram illustrating interconnected operational components of the apparatus shown in FIG. 1.

Electrical and hydraulic control systems for the evaporator 11 are shown in FIG. 4. The hydraulic system includes a pressurized air supply 41 that feeds drying gas to a manifold 42. A gas supply line including a solenoid operated air valve 43-48 is connected to each of the nozzles 22. Also connected to each nozzle 22 by a liquid supply line including a solenoid operated liquid valve 51-56 is a solvent supply manifold 49. Feeding the solvent manifold 49 is a pressurizable solvent supply bottle 58 having a pressure supply inlet 59 communicating with the air supply 41 through a solenoid operated main air valve 61.

The electrical control system for the evaporator 11 includes a plurality of microprocessors 62-64 one associated with each pair of the vessels 16. Each of the microprocessors 62-64 receives inputs from a pair of the control panel sections 26 associated with the vessels 16 to which that processor is dedicated. One pair of outputs from the microprocessor 62 are applied, respectively, to the solenoid operated gas valves 43, 44 and another pair of outputs are applied, respectively, to the solenoid operated liquid valves 51, 52. Similarly, a pair of outputs from the microprocessor 63 are applied, respectively, to the solenoid operated air valves 45, 46 and another pair of outputs are applied, respectively, to the solenoid operated liquid valves 53, 54. Finally, a pair of outputs from the microprocessor 64 are applied, respectively, to the solenoid operated air valves 47, 48 and another pair of outputs are applied, respectively, to the solenoid operated liquid valves 55, 56. An additional output of each of the microprocessors 62-64 is applied to the main solenoid evaporated air valve 61. The microprocessor 64 also receives an input from the photodetector 39 associated with the vessel 16 receiving fluid discharge from the lowermost nozzle 22 in FIG. 4. Although for reasons of space and clarity, only a single vessel 16 and sensing system 36 is shown in FIG. 4, it will be understood that each of the nozzles 22 accommodates a vessel and sensing system that provides an output to an appropriate one of the processors 62-64.

OPERATION

Typical operation of the evaporator 11 will be described in connection with the single vessel 16 shown in FIG. 4, it being understood that similar and simultaneous evaporation procedures can be occurring in all vessels. First the basin 14 is filled with conditioned water to a level preferably above the highest sample level in any of the vessels 16. Next, the control 27 is set to provide a bath temperature suitable for the process being performed. Finally, the control panel sections 26 are actuated to provide for each of the vessels 16 the desired evaporation process. Examples of selections include, for example, the number of solvent addition cycles for each vessel and whether an evaporation cycle will conclude with a sample reduction to some predetermined volume or to complete dryness.

Initially, an output from the microprocessor 62 opens the solenoid operated air valve 44 producing a flow of pressurized air from the supply 41 and the manifold 42. Resultant discharge of drying gas from the nozzle 22 produces evaporation within the vessel 16 as described above. The evaporation process will continue until the sample volume within the vessel 16 falls to a level below the light beam directed through the lower vessel portion 32 by the sensing system 36. Assuming that a minimum sample level has been selected for a termination parameter, the output from the detector 39 causes the processor 62 to provide an output that closes the air valve 44 to interrupt air flow to the nozzle 22. In the event that complete sample dryness has been selected, the processor 62 delays closing of the valve 44 for a fixed period after receiving an output signal from the photodetector 39.

If a solvent reconstitution cycle has been selected, the processor 62 provides in addition to an output to the solenoid valve 44 an output to open the normally closed main air valve 61 producing a supply of pressurized air to the inlet 59 of the solvent supply bottle 58. After a delay of, for example, five seconds to permit pressurizing of the bottle 58, the processor 62 produces an output that opens the solenoid controlled liquid valve 52. Solvent flow from the bottle 58 through the manifold 49, the valve 52 and the nozzle 22 then discharges into the vessel 16 producing the above described vessel washing cycle. The solvent discharge is produced for a predetermined time period by the processor 62. After discharge of the desired solvent volume, the processor 62 provides an output that closes the liquid valve 52 to interrupt solvent flow and provides an output that opens the air valve 44 to initiate air flow to the nozzle 22. Again, the drying gas discharged from the nozzle 22 evaporates the reconstituted sample in the vessel 16 until an output is provided by the photodetector 39 causing the microprocessor 62 to again close the air valve 44. Additional solvent reconstitution cycles will occur if selected by appropriate operation of the control panel section 26 associated with the vessel 16.

It will be noted that an output from any of the microprocessors 62-64 to the main air valve 61 occurs only in conjunction with an output to one of the solenoid operated liquid valves 51-56. Thus, in the absence of a call for solvent discharge into any of the vessels 16, the normally closed main air valve 61 remains closed. A pressurized supply of solvent from the bottle 58 is present, therefore, only during periods in which one of the liquid valves 51-56 is open in response to a reconstitution demand in one of the vessels 16. The elimination of fluid pressure in the manifold 49 during all other periods eliminates unnecessary pressure on the liquid valves 51-56 and thereby eliminates leakage problems and the hazards associated with a continuously pressurized solvent bottle.

Obviously, many modifications and variations of the present invention are possible in light of the above teachings. It is to be understood, therefore, that the invention can be practiced otherwise than as specifically described.

What is claimed:

1. Automatic apparatus for isolating solids from liquids by evaporating the liquid and comprising:
   vessel means for receiving a composition of liquid and solid substances;
   gas supply means for supplying a drying gas;
   gas line means for directing the drying gas from said gas supply means to said vessel means;
   liquid supply means for supplying a solvent capable of dissolving the solid substance;
   liquid line means for directing the solvent from said liquid supply means to said vessel means;
   sensing means for sensing liquid level conditions within said vessel means; and
   automatic control means adapted to sequentially initiate a flow of drying gas to said vessel means, initiate a flow of solvent to said vessel in response to sensing of a given liquid level condition by said sensing means, interrupt the flow of solvent to said vessel means after a certain quantity of solvent has been received thereby, and interrupt the flow of drying gas to said vessel means in response to sensing of a particular liquid level condition by said sensing means.

2. An automatic apparatus according to claim 1 including a gas valve means for controlling the flow of drying gas between said gas supply means and said vessel means; liquid valve means for controlling the flow of solvent between said liquid supply means and said vessel means; and wherein said automatic control means is operatively coupled to said gas valve means, said liquid valve means, and said sensing means, and adapted to sequentially open said gas valve means to initiate said flow of drying gas, open said liquid valve means to initiate said flow of solvent, close said liquid valve means to interrupt said flow of solvent, and close said gas valve means to interrupt said flow of drying gas.

3. An apparatus according to claim 2 wherein said control means is further adapted to close said gas valve means to interrupt the flow of drying gas to said vessel means in response to sensing of said given liquid level condition; and to open said gas valve means to initiate the flow of drying gas to said vessel means after said certain quantity of solvent has been received by said vessel means.

4. An apparatus according to claim 2 or 3 wherein said vessel means comprises a plurality of vessels, said gas valve means comprises a plurality of gas valves each adapted to control the flow of drying gas to a different one of said vessels and said liquid valve means comprises a plurality of liquid valves each adapted to control the flow of solvent to a different one of said vessels.

5. An apparatus according to claim 2 or 3 including actuator means coupled to said automatic control means and activatable thereby into either an active mode wherein said liquid supply means provides pressurized solvent to said liquid valve means or an inactive mode wherein said liquid supply means fails to provide pressurized solvent to said liquid valve means, and said control means is further adapted to produce said active mode during substantially all periods in which said liquid valve means is open and to produce said inactive mode during substantially all periods in which said liquid valve means is closed.

6. An apparatus according to claim 5 wherein said vessel means comprises a plurality of vessels, said gas valve means comprises a plurality of gas valves each adapted to control the flow of drying gas to a different one of said vessels and said liquid valve means comprises a plurality of liquid valves each adapted to control the flow of solvent to a different one of said vessels.

7. An apparatus according to claim 3 including a nozzle means for discharging fluid into said vessel means; and said nozzle means is in fluid communication with both said gas line means and said liquid line means so as to receive therefrom, respectively, either drying gas or solvent for discharge into said vessel means.

8. An apparatus according to claim 7 wherein said vessel means comprises a plurality of vessels, said gas valve means comprises a plurality of gas valves each adapted to control the flow of drying gas to a different one of said vessels, and said nozzle means comprises a plurality of nozzles each disposed for discharge into a different one of said vessels.

9. An apparatus according to claim 5 wherein said liquid supply means comprises a pressurizable supply container having a pressure inlet and a discharge outlet connected to said liquid valve means, and said actuator means comprises a pressure valve adapted to provide pressure at said inlet in said active mode and to eliminate pressure at said inlet in said inactive mode.

10. An apparatus according to claim 9 wherein said pressure valve is connected for fluid communication between said inlet and said gas supply means.

11. An apparatus according to claim 10 wherein said vessel means comprises a plurality of vessels, said gas valve means comprises a plurality of gas valves each adapted to control the flow of drying gas to a different one of said vessels and said liquid valve means comprises a plurality of liquid valves each adapted to control the flow of solvent to a different one of said vessels.

12. Apparatus for isolating solids from liquids by evaporating the liquid and comprising:
    support means;
    a tubular vessel supported by said support means, having an opening at the top thereof, and forming a chamber for receiving a liquid composition to be dried to a suitably dry state; said vessel comprising an upper tubular portion with a substantially uniform given cross-section having one area and a lower tubular portion with a substantially uniform predetermined cross-section having an area substantially smaller than said one area;
    gas supply means;
    gas lines means for directing evaporating gas from said supply means through said opening into said upper portion of said vessel;
    source means disposed to direct a beam of radiation through said lower portion of said vessel;
    radiation detector means disposed to receive said beam of radiation directed through said lower portion of said vessel; and
    electrical control means for controlling the flow of drying gas between said supply means and said gas lines in response to the level of radiation detected by said detector means.

13. An apparatus according to claim 12 wherein said electrical control means is adapted to interrupt the flow of drying gas between said gas supply means and said gas line in response to a substantial change in the level of radiation detected by said detector means.

14. An apparatus according to claim 12 wherein said upper tubular portion of said vessel has a length substantially greater than said lower tubular portion.

* * * * *